United States Patent [19]
Kossoff

[11] 3,939,696
[45] Feb. 24, 1976

[54] SCANNING ULTRASONIC INSPECTION METHOD AND APPARATUS

[75] Inventor: George Kossoff, Northbridge, Australia

[73] Assignee: The Commonwealth of Australia, Australia

[22] Filed: June 8, 1973

[21] Appl. No.: 368,357

[30] Foreign Application Priority Data
June 8, 1972 Australia............................. 9262/72
May 1, 1973 Australia............................. 3143/73

[52] U.S. Cl. .............................................. 73/67.8 S
[51] Int. Cl.² ........................................ G01N 29/04
[58] Field of Search............. 73/67.8 R, 67.8 S, 67.9

[56] References Cited
UNITED STATES PATENTS
| 3,023,611 | 3/1962 | Howry .............................. 73/67.8 S |
| 3,086,195 | 4/1963 | Halliday ........................ 73/67.8 UX |
| 3,439,530 | 4/1969 | Flaherty et al. ................... 73/67.8 S |

Primary Examiner—Donald O. Woodiel
Assistant Examiner—John P. Beauchamp

[57] ABSTRACT

Apparatus for pulse-echo ultrasonic examination, particularly in medical diagnostic examination, is comprised of a plurality of transducers spaced at fixed positions around the object to be examined, each of the transducers being steerable to direct pulses of ultrasonic energy into the object and to receive echoes in a plurality of angular directions from the fixed position.

4 Claims, 6 Drawing Figures

General Schematic

FIG.4 General Schematic

Transmitter & Receiver Switching

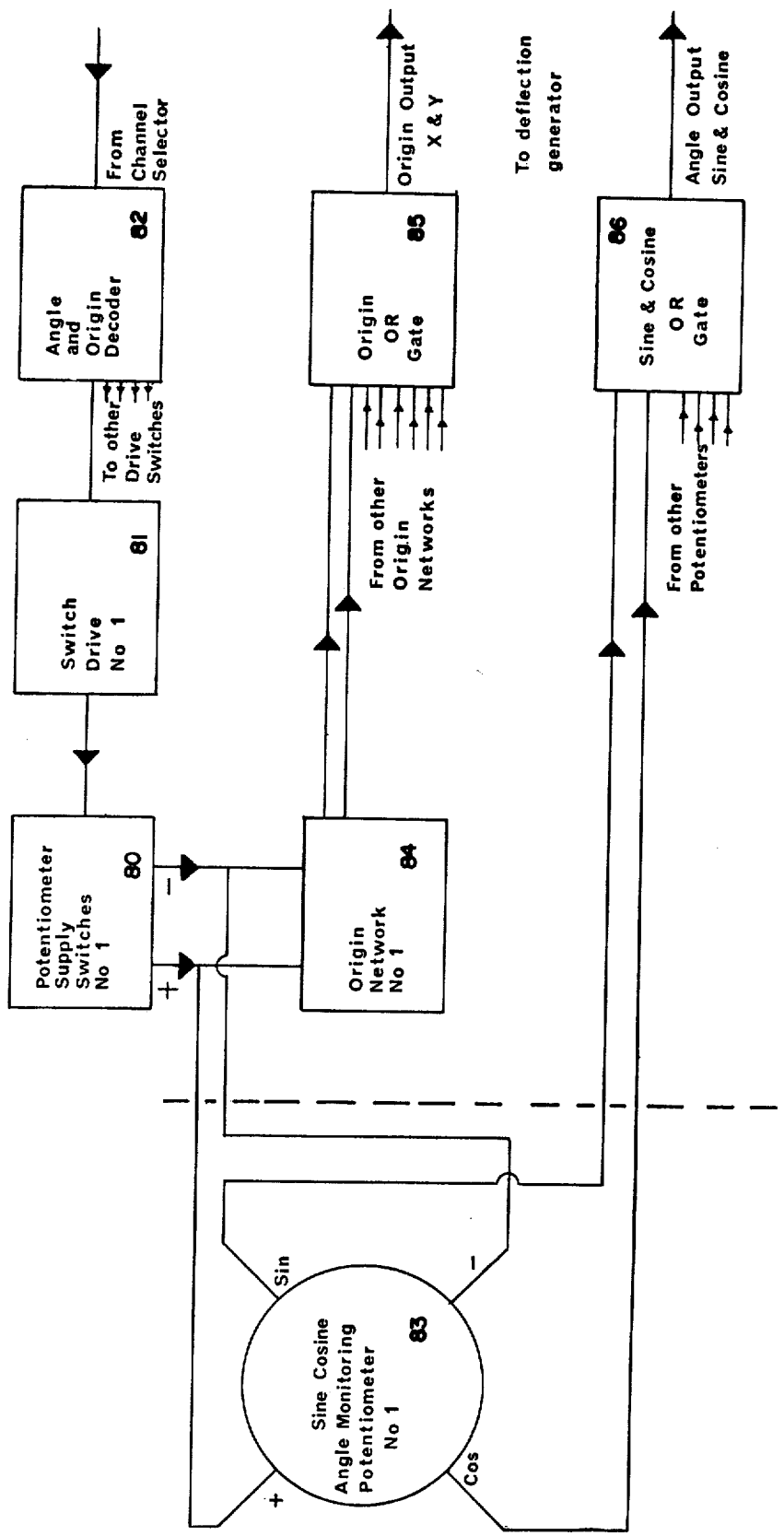

SCANNING ULTRASONIC INSPECTION METHOD AND APPARATUS

This invention relates to the technique of ultrasonic echoscopy of objects and in particular to means for decreasing the time required for examination of an object using the pulse-echo ultrasonic technique. It is particularly, but not solely, directed to the use of this technique in medical diagnostic examination.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range, into the examined object where any acoustic impedance discontinuities in the object reflect and return some of the energy in the form of an echo. This echo is received, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed for example as a deflection of the base line or as an intensity change. In a two dimensional display, the position along a base line is used to indicate the distance to the reflecting surface as in a one dimensional display, and the direction of the baseline is used to represent the direction of propagation of the acoustic energy. The two dimensional display is obtained by changing this direction of propogation of the acoustic energy and by instituting a similar but not necessarily identical movement of the base line of the display. The magnitude of the echo is displayed as for a one dimensional display, for example, as a deflection of the base line or as an intensity change.

The technique of ultrasonic echoscopy is used in medical diagnosis to obtain information about the anatomy of patients. The application of this technique is now widely investigated and is described, for example, by D.E. Robinson in Proceedings of the Institution of Radio and Electronics Engineers Australia, Vol. 31, No. 11, pages 385–392, November, 1970: "The Application of Ultrasound in Medical Diagnosis." As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart, these being areas of soft tissue with little bone and air. In general, the technique is considered to complement other techniques to provide a more complete picture of the patients' condition, however, particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

In the presently known forms of ultrasonic diagnostic examination, a single transducer is used and it is physically moved to various positions around the patient. At each of these positions the beam is swept with an oscillatory motion while constrained to remain within a single plane by mechanical oscillation of the transducer, to obtain the required scan pattern. By the use of suitable deflection circuits, for example, in a cathode ray display tube, a line is caused to follow the motions of the beam axis and echoes within the part examined are thus displayed in their correct geometrical positions. By way of example, for transverse sections, the transducer may be moved horizontally in a 150° arc around a patient who is substantially erect while undergoing ± 15° oscillations and for longitudinal sections the transducer may be moved vertically while undergoing ± 30° oscillations.

It has, however, been found that in such systems where the transducer is physically moved around the patient this movement leads to a limitation on the examination time of between ten and twenty seconds for each cross-sectional visualisation due to mechanical inertia and, in the case where the transducer is coupled to the patient via a coupling medium such as water, the generation of turbulance by the transducer when it moves quickly in the coupling medium.

It is a primary object of the present invention to provide apparatus for and a method of ultrasonic examination of an object which will avoid the limitations discussed above and thus enable a speeding up of the time required for each cross-sectional visualisation. It will be apparent that a reduction in examination time of a patient will lead to a technical improvement in the resultant echograms as the effects of movement of the part under examination will be reduced. In addition, a reduction in examination time of a patient will have the economic advantage that more cross-sectional visualisations and hence more examinations will be able to be performed in a given time.

According to the present invention there is provided apparatus for the ultrasonic examination of an object comprising a plurality of transducers, each transducer being capable of directing pulses of ultrasonic energy along a beam into the said object and receiving echoes of said pulses reflected along said beam by acoustic impedance discontinuities in said object, the said transducers being spatially positioned relative to each other and to the said object and the beam from each transducer being steerable to a plurality of angular directions in a single plane.

In another aspect, this invention provides a method of ultrasonic examination of an object which comprises directing pulses of ultrasonic energy along a plurality of beams into said object and receiving echoes of said pulses reflected along said beams by acoustic impedance discontinuities in said object, the said beams being directed into the object from positions spaced relative to each other and each beam being steerable to a plurality of angular directions in a single plane.

The present invention therefore involves the use of a number of transducers instead of the single transducer previously used. These may be any type of electromechanical transducer. The physical movement of the single transducer, for example, around the patient, in the prior art is replaced by providing a number of transducers around the patient which are switched appropriately to obtain the required scan pattern. It is necessary that the beam axes of the plurality of transducers of the present invention be oscillated in order that a composite cross-sectional visualisation can be built up and this oscillatory motion may be provided by two alternative means.

The first means of obtaining oscillatory motion of the beam axes is by mechanically scanning all of the plurality of transducers simultaneously. In this case, although mechanical movement of the transducers does introduce a limitation on the scanning rate, the present invention enables the effect of this limitation to be minimised by providing suitable switching means which require the transducers to scan only once while obtaining a complete cross-sectional visualisation. An important feature of the present invention then comprises activating each transducer in turn to direct a pulse of ultrasonic energy along its beam axis and receive echoes reflected back along the beam axis, the rate at which the transducers are activated being sufficiently fast, compared with the rate of mechanical oscillation of the transducers, that each transducer oscillates only a small distance between successive activations thereof. The final result achieved by this method of operation is that at the end of a single mechanical scan, each of the transducers has been activated whilst its beam was directed in all required directions.

The alternative means of obtaining oscillatory motion of the beam axes is by use of transducer arrays at each transducer position, the arrays being appropriately designed as to be capable of being steered electronically. In such a system there are no moving parts and the scanning rate obtainable with this system is limited only by considerations of electronic switching speeds and the rate of acquisition of ultrasonic information by the transducer after each transmitted pulse. Since such an array may be electronically steered to direct its beam in all required directions at a rate much faster than that possible when mechanical oscillation of the transducer is required, it is possible to operate this system by steering the beam from each transducer array to each of the required directions to measure the reflected echos before activating the next transducer array and steering the beam from it to each of the required directions, and so on. It will, however, be appreciated that this plurality of transducer arrays capable of being electronically steered may also be operated in a manner similar to the operation of the mechanically oscillated transducers previously described.

That is, when the plurality of transducers are transducer arrays, such as to be capable of being electronically steered instead of the beam from each transducer array being steered to each of the required directions before activating the next array, each of the arrays may be activated sequentially in one of the required directions in a manner analagous to the method of operation when using mechanically scanned transducers.

Other objects and features of the invention are illustrated in the accompanying drawings in which:

FIG. 6 shows a block diagram of an angle and origin switching network.

Figure 1:
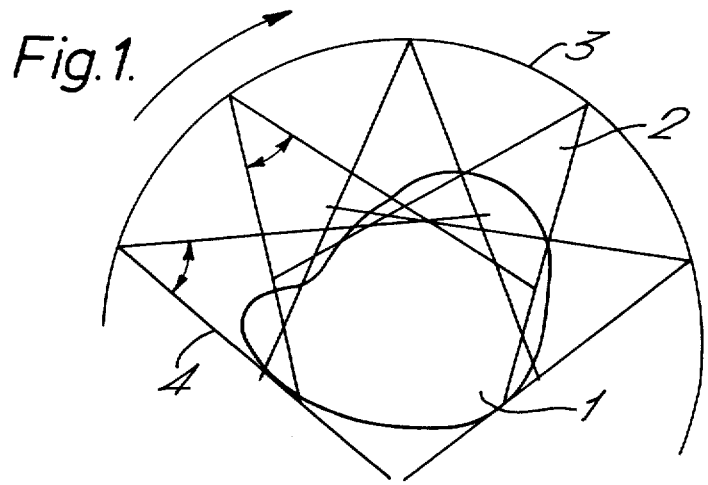
FIG. 1 is a schematic representation illustrating the operation of known apparatus for ultrasonic examination.

The current technique is illustrated in FIG. 1 in which area 1 denotes the outline of the structure under examination, area 2 denotes the water coupling tank and arc 3 denotes the path of motion of the single examining transducer. As the transducer traverses path 3 it performs an oscillatory motion with usually about 10 of the oscillatory motions for each traverse of path 3. Thus the structure 1 is viewed from a multiplicity of positions and directions during the scanning procedure and at each of these positions a pulse of ultrasonic energy is directed into the structure and reflected echoes received.

Figure 2:
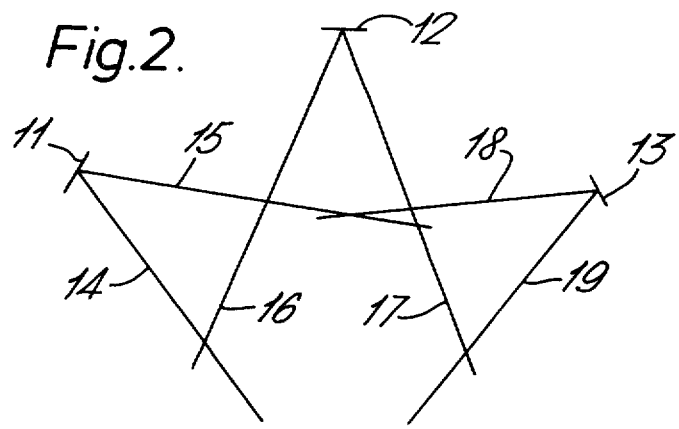
FIG. 2 is a schematic representation illustrating the operation of a first embodiment of the apparatus for ultrasonic examination according to the present invention.

The first embodiment of this invention is shown in FIG. 2 in which for clearer illustration only three transducers are used, although it will be understood that any suitable number, for example, eight may be used. In this case the transducers 11, 12 and 13 consist of multi-element arrays which may be steered electronically. The electronically steered beam 14 from transducer 11 is first used and the beam then moved a small angle at a time until it gets to beam direction 15. The equipment is then switched to transducer 12 and the beam swept from beam 16 to beam 17. The procedure is repeated with transducer 13 and beams 18 and 19. At each position between 14 and 15, 16 and 17, 18 and 19, the appropriate transducer 11, 12 and 13 respectively is activated to direct a pulse of ultrasonic energy into the structure under examination and to receive reflected echoes.

Figure 3:
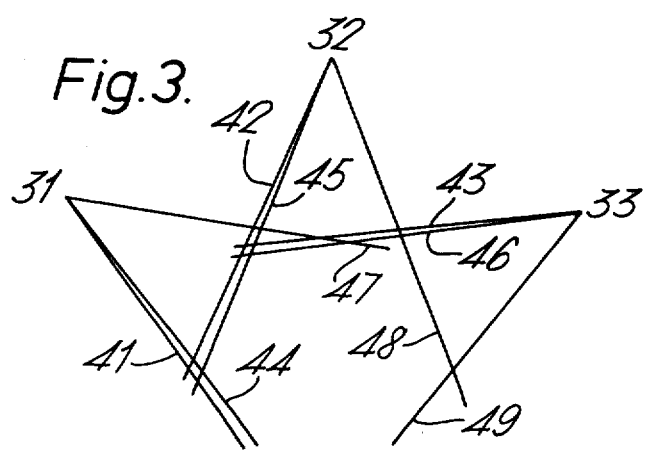
FIG. 3 is a schematic representation illustrating the operation of a second embodiment of the apparatus of the present invention.

The second embodiment of this invention utilises mechanically scanned transducers and the operation of this embodiment is illustrated in FIG. 3 in which the mechanically scanned transducers 31, 32 and 33 initially point in directions 41, 42 and 43. Transducer 31 is activated and a pulse directed and echoes received along beam axis 41. Transducer 32 is then activated and a pulse directed and echoes received along beam 42 and then similarly with transducer 33 and beam 43. The transducers are then moved to beam axis positions 44, 45 and 46.

A pulse is directed and echoes received first at transducer 31 along beam direction 44 and then on the other corresponding beams. The procedure is repeated until the beam directions 47, 48 and 49 are reached, at which time a complete scan of the structure under examination has been performed with only one cycle of mechanical oscillation from the set of transducers. As previously described, this method of sequentially activating the transducers may also be used with the transducer arrays discussed in connection with FIG. 2. The signals obtained in accordance with either of the embodiments of FIG. 2 or FIG. 3 may be processed and displayed as a cross-sectional or other visualisation of the structure examined.

Figure 4:
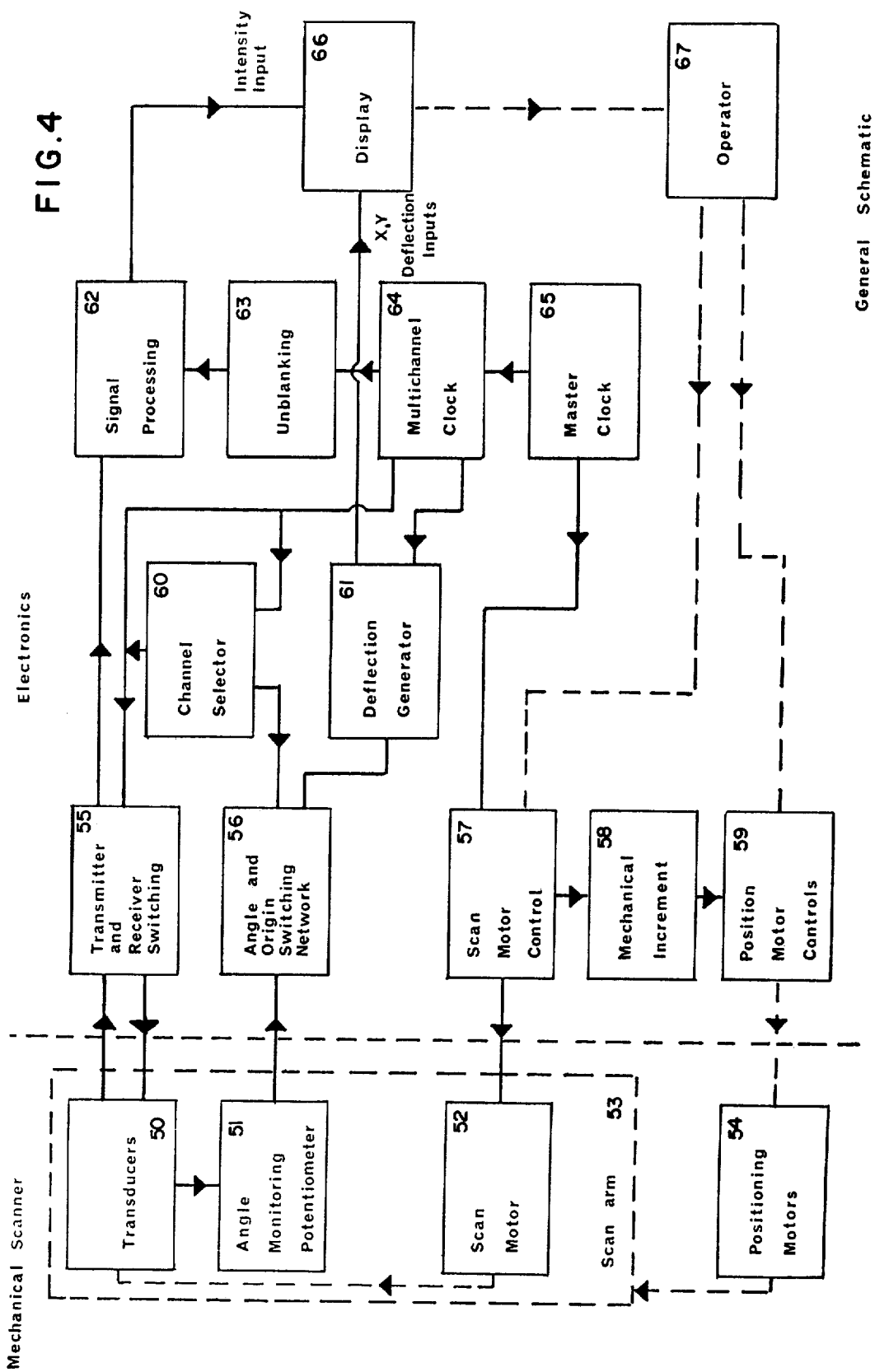
FIG. 4 shows a basic block diagram of one form of the electronics for the ultrasonic transducer array according to the subject invention.

As shown in FIG. 4 the plurality of transducers 50 used to acquire the ultrasonic information are mounted on a scan arm assembly shown schematically by box 53. Also carried on the scan arm assembly are angle monitoring potentiometers 51 and the transducers are scanned as described above by scan motor 52. The position of the plane which is to be scanned by the apparatus is set by the position of the scan arm 53. This is adjusted by positioning motors 54 which are controlled by positioning motor controls 59 under the direction of operator 67. In the positioning control system there may be included a system such that the mechanism automatically moves to a new scan plane at the end of each scan. This may be achieved by operator 67 setting scan motor control 57 appropriately and at the end of each scan, mechanical increment 58 will apply a pulse to position motor controls 59 to achieve the mechanical increment.

The master clock 65 provides basic time impulses to initiate multi-channel clock 64 and to drive motors 52 and 54 via the motor controls 57 and 59.

The multi-channel clock 64 outputs, in turn, trigger pulses to each channel upon receiving a pulse from the master clock 65.

The channel selector 60 counts trigger pulses and sends a binary channel address code to transmitter and receiver switching network 55 and to angle and origin switching network 56.

The signal processer 62 processes echoes from transmitter and receiver switching network 55, which echo signals are fed together with blanking pulses from blanking circuit 63 to the intensity modulation input of the display unit 66.

Deflection generator 61 generates X and Y deflection voltages from signals received from angle and origin switching network 56.

Figure 5:
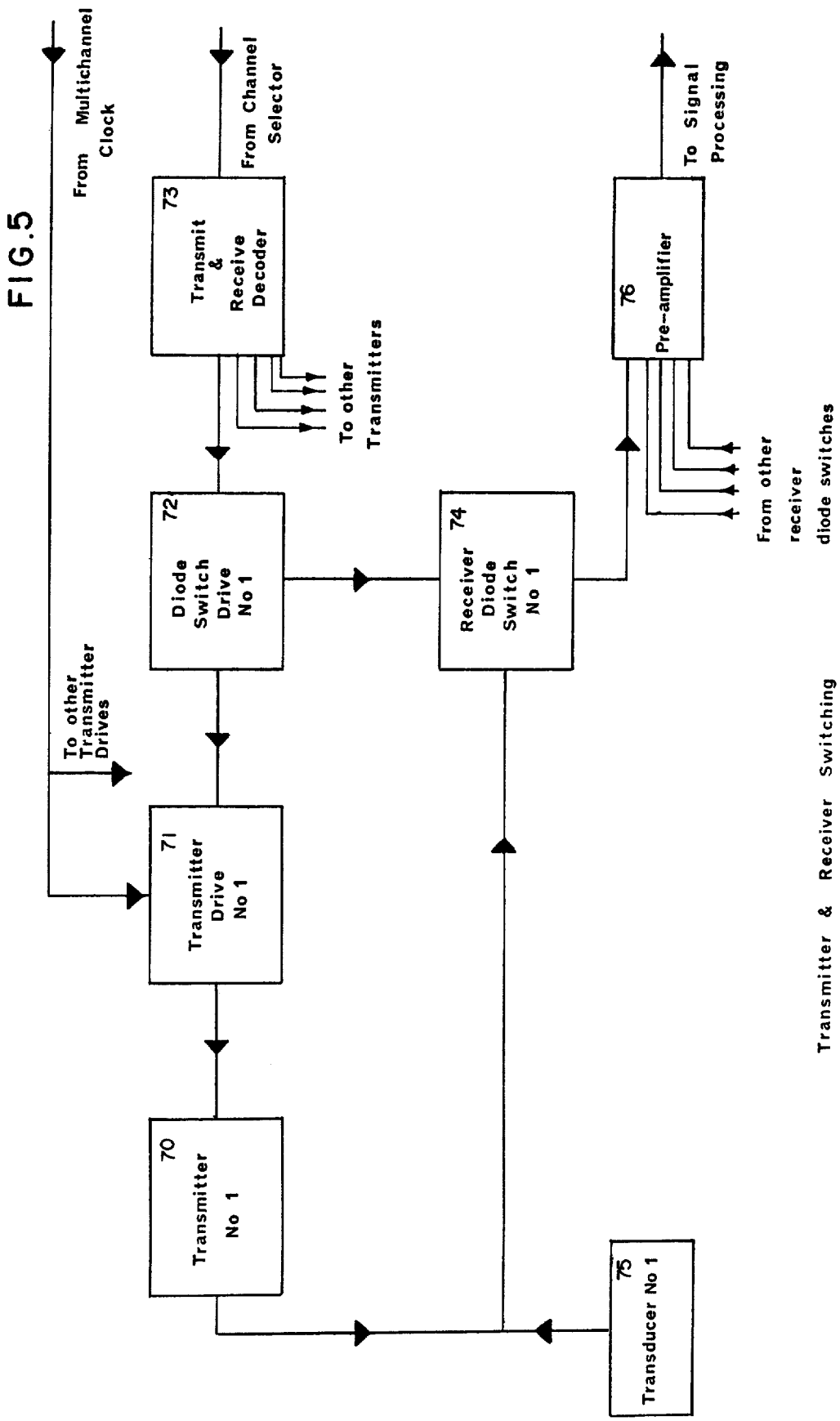
FIG. 5 shows a transmitter and receiver switching block diagram.

FIG. 5 shows transmitter and receiver switching network in greater detail. As seen in FIG. 5, transmit and receive decoder 73 decodes channel selector output signals from channel selector 60 to activate the correct diode switch drive 72 and transmitter drive 71. The multi-channel clock output then triggers the transmitter drive 71 to energize the transmitter 70.

Receiver diode switch 74 is energized by the decoder 73 via diode switch drive 72 which allows echo signals to pass to the preamplifier 76.

In FIG. 6, the angle and origin switching network 56 of FIG. 4 is more fully disclosed. As seen in FIG. 6, angle and origin decoder 82 decodes the channel selector output to activate the correct switch drive 81 and hence turn on the correct potentiometer supply switch 80. The supply switch 80 supplies reference voltages to the sine cosine angle monitoring potentiometer 83 and to the origin network 84.

The X and Y origin coordinates from the origin network 84 and the sine and cosine angle output from the potentiometer 83 are fed via their respective OR gates to the deflection generators 61 (see FIG. 4) within the processing electronics.

From the foregoing description it will therefore be appreciated that the present invention enables more rapid scanning of an object subject to ultrasonic examination. While the invention has been described with reference to preferred embodiments, it will be generally understood by those skilled in the art that various changes may be made and equivalents be substituted for elements thereof without departing from the true spirit and scope of the invention. The claims defining the invention are as follows:

I claim:

1. Apparatus for the ultrasonic examination of an object comprising a plurality of transducers for directing pulses of ultrasonic energy along a beam into the said object and receiving echoes of said pulses reflected along said beam by acoustic impedance discontinuities in said object, said transducers being spatially positioned relative to each other and to the said object, means for simultaneously mechanically moving said transducers to steer each of said beams to a plurality of angular directions in a single plane, and means for sequentially activating each of said transducers to direct a pulse of ultrasonic energy along a beam into the object and to receive echoes reflected along said beam in each of said angular directions at a rate sufficiently fast, compared to the rate of mechanical movement of the transducers, that the beam of each transducer moves only a small distance between successive activations thereof.

2. Apparatus for the ultrasonic examination of an object comprising a plurality of transducers for directing pulses of ultrasonic energy along a beam into the said object and receiving echoes of said pulses reflected along said beam by acoustic impedance discontinuities in said object, said transducers being spatially positioned relative to each other and to the said object, means for electronically steering each of said beams to a plurality of angular directions in a single plane, and means for sequentially activating each of said transducers to direct a pulse of ultrasonic energy along a beam into the object and receive echoes reflected along said beam in each of said angular directions at a rate sufficiently fast, compared to the rate of movement of the transducer beams, that the beam of each transducer moves only a small distance between successive activations thereof.

3. Apparatus as claimed in claim 2, characterized in that each of said plurality of transducers comprises a multi-element array.

4. A method of ultrasonic examination of an object which comprises directing pulses of ultrasonic energy along a plurality of beams into said object, and receiving echoes of said pulses reflected along said beams by acoustic impedance discontinuities in said object, said directing step including:

directing said beams into the object from positions spaced relative to each other;

steering said beams to a plurality of angular directions in a single plane; and directing said pulses sequentially along each of said beams in each of said angular positions at a rate sufficiently fast, compared to the rate of movement of the transducer beams; that the beam of each transducer moves only a small distance between successive activations thereof.

* * * * *